(12) United States Patent
Rosinger et al.

(10) Patent No.: US 7,981,838 B2
(45) Date of Patent: Jul. 19, 2011

(54) DEFOLIANT

(75) Inventors: Christopher Rosinger, Hofheim (DE); Frank Ziemer, Kriftel (DE); Udo Bickers, Wietmarschen (DE)

(73) Assignee: Bayer CropScience AG, Monheim (DE)

( * ) Notice: Subject to any disclaimer, the term of this patent is extended or adjusted under 35 U.S.C. 154(b) by 503 days.

(21) Appl. No.: 12/108,945

(22) Filed: Apr. 24, 2008

(65) Prior Publication Data

US 2008/0269056 A1   Oct. 30, 2008

(30) Foreign Application Priority Data

Apr. 25, 2007 (EP) .................. 07008372

(51) Int. Cl.
*A01N 43/00* (2006.01)
*A01N 25/32* (2006.01)
*A01N 41/02* (2006.01)

(52) U.S. Cl. .............. 504/166; 504/111; 504/162

(58) Field of Classification Search ........... 504/166, 504/111, 139, 162
See application file for complete search history.

(56) References Cited

U.S. PATENT DOCUMENTS

| 4,261,726 A | 4/1981 | Rusch et al. |
| 4,613,354 A | 9/1986 | Rusch |
| 5,215,570 A | 6/1993 | Burckhardt et al. |
| 6,235,680 B1 | 5/2001 | Ziemer et al. |
| 6,251,827 B1 | 6/2001 | Ziemer et al. |
| 6,274,535 B1 | 8/2001 | Feurer et al. |
| 2007/0010399 A1* | 1/2007 | Rosinger et al. ............ 504/111 |

FOREIGN PATENT DOCUMENTS

| AU | 624730 | 6/1992 |
| DE | 19911165 | 9/2000 |
| EP | 0 412 364 B1 | 2/1991 |
| WO | 99/16744 | 4/1999 |

OTHER PUBLICATIONS

Krogmeier, M., Phytotoxicity of Foliar-Applied Urea, Nov. 1989, Proc. National. Acad. of Science, vol. 86, pp. 8189-8191.*
International Search Report of PCT/EP2008/002856, dated Sep. 24, 2008 (3 pages).

* cited by examiner

*Primary Examiner* — Johann Richter
*Assistant Examiner* — Andriae M Holt
(74) *Attorney, Agent, or Firm* — Baker Donelson Bearman, Caldwell & Berkowitz, PC

(57) ABSTRACT

A mixture, which comprises
(A) thidiazuron (or thidiazuron and diuron), and
(B) one or more compounds from the group of the N-phenyl-sulfonyl(het)arylamides, if appropriate also in salt form, of the formula below:

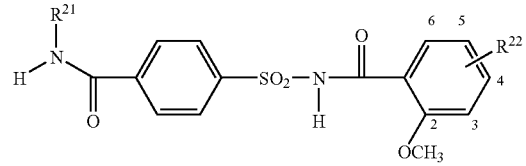

in which
$R^{21}$ is cyclopropyl and $R^{22}$ is H,
$R^{21}$ is cyclopropyl and $R^{22}$ is 5-Cl,
$R^{21}$ is ethyl and $R^{22}$ is H,
$R^{21}$ is isopropyl and $R^{22}$ is 5-Cl or
$R^{21}$ is isopropyl and $R^{22}$ is H;
is suitable for use as a defoliant, in particular in crops of cotton.

14 Claims, No Drawings

DEFOLIANT

CROSS REFERENCE TO RELATED APPLICATIONS

This application claims priority from EP 07 008 372.0 filed Apr. 25, 2007, the content of which is incorporated herein by reference.

BACKGROUND OF THE INVENTION

1. Field of the Invention

The invention relates to the field of defoliants, in particular thidiazuron-containing mixtures, and their use in crops of cotton.

2. Description of Related Art

Thidiazuron has been known for some time as a defoliant, in particular for use in crops of cotton (see, for example, "The Pesticide Manual", 14th edition, British Crop Protection Council, Hampshire 2006).

The use of thidiazuron in mixtures has also been described, see, for example, DE 26 46 712 A.

However, since the economical and ecological demands placed on modern defoliants are constantly being raised, for example with respect to effect, application rate, residues, toxicity and favorable manufacturing, there exists the permanent task of developing, for example by combining known active ingredients, novel defoliants which offer, at least in some areas, advantages compared with the known compounds.

SUMMARY OF THE INVENTION

Surprisingly, it has been found that thidiazuron and already commercially used mixtures of thidiazuron and diuron in a mixture with compounds from the group of the N-phenylsulfonyl(het)arylamides have synergistic effects.

The present invention accordingly provides a mixture which comprises
(A) thidiazuron or thidiazuron and diuron, and
(B) one or more compounds from the group of the N-phenylsulfonyl(het)arylamides, if appropriate also in salt form, of the formula below:

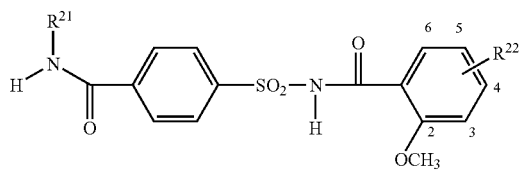

in which
$R^{21}$ is cyclopropyl and $R^{22}$ is H,
$R^{21}$ is cyclopropyl and $R^{22}$ is 5-Cl,
$R^{21}$ is ethyl and $R^{22}$ is H,
$R^{21}$ is isopropyl and $R^{22}$ is 5-Cl or
$R^{21}$ is isopropyl and $R^{22}$ is H.

The mixtures according to the invention are suitable in particular for use as defoliants in crops of cotton, due, for example, to rapid action and/or increased activity or lower application rates.

DETAILED DESCRIPTION OF A PREFERRED EMBODIMENT

For the purpose of the invention, the term defoliant is synonymous with "desiccant" and also embraces the known growth-regulating effect of thidiazuron and mixtures comprising thidiazuron.

The active ingredients (a.i.) thidiazuron and diuron used for component (A) are known and commercially available: thidiazuron and diuron from Bayer CropScience, Germany.

Mixtures of thidiazuron and diuron are commercially available, for example, under the name Dropp Ultra® (Bayer CropScience). Such mixtures are described, for example, in U.S. Pat. No. 4,613,354 A.

The active ingredients, with specifications about their preparation, mixing and handling, are described, for example in "The Pesticide Manual", 14th edition (see above), and they are listed under the following entry numbers: Thidiazuron 814, Diuron 291. The preferred component (A) is thidiazuron.

The compounds that can be used for component (B) from the group of the N-phenylsulfonyl(het)arylamides belong to a chemical class which is described, for example, in EP 365484 A1, WO 97/45016 A1, WO 99/16744 A1 or U.S. Pat. No. 6,251,827 B1, and of which, for example, some representatives are known for their action as safeners. One representative of this chemical class is, for example, the active compound cyprosulfamide (Bayer CropScience).

The group of the N-phenylsulfonyl(het)arylamides is characterized by,
if appropriate also in salt form, compounds of the formula below:

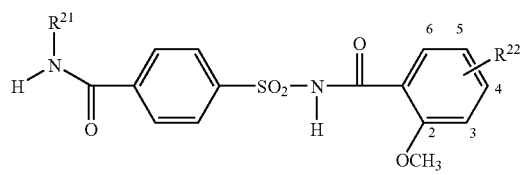

in which
$R^{21}$ is cyclopropyl and $R^{22}$ is H (4-cyclopropylaminocarbonyl-N-(2-methoxybenzoyl)benzenesulfonamide; cyprosulfamide),
$R^{21}$ is cyclopropyl and $R^{22}$ is 5-Cl,
$R^{21}$ is ethyl and $R^{22}$ is H,
$R^{21}$ is isopropyl and $R^{22}$ is 5-Cl or
$R^{21}$ is isopropyl and $R^{22}$ is H (4-isopropylaminocarbonyl-N-(2-methoxybenzoyl)benzenesulfonamide).

Salt form means that the compound in question, depending on its acidity or basicity, is present, for example after action of a base or an acid, in the form of the corresponding salt. Examples of salts are those having alkaline earth metal ion, alkali metal ion and ammonium as cation. Preference is given to the sodium and potassium salts. Other examples of salts are hydrochlorides.

Preferred as component (B) are the compounds 4-cyclopropylaminocarbonyl-N-(2-methoxybenzoyl)benzenesulfonamide (cyprosulfamide) and 4-isopropylaminocarbonyl-N-(2-methoxybenzoyl)benzenesulfonamide; particularly preferred as component (B) is cyprosulfamide.

In principle, the application can also be carried out by successive applications of the individual active ingredients (components), where the possible interval can be determined in simple routine preliminary trials. However, preference is given to joint application. If appropriate, the active ingredients can also be used in combination with other crop protection agents.

While having the same effect, the application rate of an individual active ingredient in the combination is considerably reduced compared with the application rate of the individual active ingredient in question when used on its own. The optimum choice of the ratio by weight and the application rates depends, for example, on the development stage, on environmental factors and climatic conditions or else on the type of the active crop-protective agents which are additionally employed, if appropriate, and can be determined quickly by the person skilled in the art in simple routine trials.

The application rate for component (A) is generally in the range from 1 to 500 g of active ingredient (=a.i.)/ha.

For thidiazuron, it is preferably in the range from 10 to 500 g of a.i./ha, particularly preferably from 10 to 300 g of a.i./ha, very particularly preferably from 20 to 200 g of a.i./ha, especially preferably from 20 to 150 g of a.i./ha.

In the case of thidiazuron/diuron mixtures (typically in a ratio by weight of 2:1), the application rate is in the general range from 10 to 500 g of a.i./ha, preferably at from 15 to 300 g of a.i./ha, particularly preferably in the range from 20 to 200 g of a.i./ha, particularly preferably from 30 to 200 g of a.i./ha, in particular from 30 to 150 g of a.i./ha.

The application rates for the component (B) can vary within wide limits, depending on the active ingredient, and they are generally between 0.1 and 5000 g of a.i./ha.

Preferred application rates for the component (B) are, for example (cyprosulfamide): from 1 to 1000 g of a.i./ha, particularly preferably from 5 to 500 g of a.i./ha.

The ratios by weight of components (A):(B) can vary within wide limits; in general they are between 1:100 and 100:1.

The approximate ratio of (A):(B) is preferably 1:0.1-10, particularly preferably 1:0.5-2.

The invention also provides defoliants, i.e. compositions for effecting leaf abscission, which defoliants comprise combinations of active ingredients (A) and (B) and customary formulation auxiliaries (C).

The combinations according to the invention and their individual active ingredients can be formulated in various ways, depending on the prevailing biological and/or chemico-physical parameters. Examples of possible suitable formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, solutions which are miscible with oils, capsule suspensions (CS), dusts (DP), granules (GR) in the form of microgranules, spray granules, coated granules and adsorption granules, water-dispersible granules (WG), water-soluble granules (SG), ULV (ultra-low-volume) formulations, microcapsules and WSBs (water-soluble bags).

The individual types of formulation are known in principle and are described, for example, in: Winnacker-Küchler, "Chemische Technologie" [Chemical Technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

Based on these formulations, it is also possible to prepare combinations with other crop protection agents, such as, for example, insecticides, acaricides, herbicides, fungicides, safeners, other growth regulators and/or fertilizers, for example in the form of a ready mix or a tank mix.

In addition, depending on the intended application, it may also be advantageous to add, separately, further formulation auxiliaries (C) and/or further additives, such as, for example, nonionic wetting agents, e.g. Agrotin®, from Bayer CropScience.

Wettable powders are preparations which are uniformly dispersible in water and which, besides the active ingredient, also comprise ionic and/or nonionic surfactants (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalene-sulfonate or else sodium oleoylmethyltaurinate, in addition to a diluent or inert substance. To prepare the wettable powders, the active ingredients are ground finely, for example in customary equipment such as hammer mills, blower mills and air-jet mills, and simultaneously or subsequently mixed with the formulation auxiliaries.

Emulsifiable concentrates are prepared by dissolving the active ingredients in an organic solvent, for example butanol, cyclohexanone, dimethylformamide, xylene, or else higher-boiling aromatics or hydrocarbons, or mixtures of the organic solvents with the addition of one or more ionic and/or nonionic surfactants (emulsifiers). Examples of emulsifiers which can be used are: calcium salts of alkylarylsulfonic acid such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters or polyoxyethylene sorbitan esters, for example polyoxyethylene sorbitan fatty acid esters.

Dusts are obtained by grinding the active ingredients with finely divided solid substances, for example talc, natural clays such as kaolin, bentonite and pyrophyllite, or diatomaceous earth. Suspension concentrates can be water- or oil-based. They can be prepared, for example, by wet grinding using commercially available bead mills with or without addition of surfactants as have already been mentioned above, for example in the case of the other types of formulation.

Emulsions, for example oil-in-water emulsions (EW), can be prepared, for example, by means of stirrers, colloid mills and/or static mixers using aqueous organic solvents and, if appropriate, surfactants as have already been mentioned above, for example in the case of the other types of formulation.

Granules can be prepared either by spraying the active ingredients onto adsorptive granulated inert material or by applying active ingredient concentrates to the surface of carriers such as sand, kaolinites or of granulated inert material by means of binders, for example polyvinyl alcohol, sodium polyacrylate or else mineral oils. The active ingredients can also be granulated in the manner which is conventional for the production of fertilizer granules, if desired in a mixture with fertilizers.

Water-dispersible granules are generally prepared by the customary methods such as spray-drying, fluidized-bed granulation, disk granulation, mixing with high-speed mixers and extrusion without solid inert material.

In general, the mixtures according to the invention comprise 0.1 to 99% by weight, in particular 0.1 to 95% by weight, of active ingredients of the components (A) and/or (B).

The active ingredient concentration in wettable powders is, for example, approximately 10 to 90% by weight, the remainder to 100% by weight being composed of customary formulation components. In the case of emulsifiable concentrates, the active ingredient concentration may amount to approximately 1 to 90% by weight. Formulations in the form of dusts comprise, for example, 1 to 80% by weight of active ingredient, in most cases 5 to 60% by weight of active ingredient. Sprayable solutions comprise, for example, 0.05 to 80% by weight, in most cases 2 to 50% by weight, of active ingredient. The active ingredient content of water-dispersible granules depends partly on whether the active compound is in liquid or solid form and on which granulation auxiliaries, fillers and the like are being used. The active ingredient content of the water-dispersible granules amounts to, for example, between 1 and 95% by weight, in most cases between 10 and 80% by weight.

In addition, the abovementioned formulations of active ingredients comprise, if appropriate, adhesives, wetting agents, dispersants, emulsifiers, penetrants, preservatives, antifreeze agents, solvents, fillers, carriers, colorants, antifoams, evaporation inhibitors and pH and viscosity regulators, which are customary in each case.

Components which can also be used in combination with the active ingredients according to the invention in mixed formulations or in a tank mix are, for example, known active ingredients as are described, for example, in Weed Research 26, 441-445 (1986), or "The Pesticide Manual", 14th edition, (see above), and the literature cited therein.

For use, the formulations, which are in commercially available form, are, if appropriate, diluted in the customary manner, for example using water in the case of wettable powders, emulsifiable concentrates, dispersions and water-dispersible granules, and then applied to the plants. This includes specific application variants customary in cotton cultivation, for example the application by airplane. Preparations in the form of dusts, granules for soil application or for broadcasting and also sprayable solutions are conventionally not diluted any further with other inert substances prior to use.

The invention also provides the use of the components of the compositions or mixtures according to the invention as defoliants, i.e. for effecting leaf abscission in plants, preferably in suitable crops of useful plants, such as cotton, sunflowers or potatoes. Particular preference is given to the use as defoliant in crops of cotton.

The invention also provides a method for defoliating a plant, preferably a useful plant, particularly preferably a cotton plant, wherein the plant is treated with the components of a mixture according to the invention or a composition according to the invention.

The mixtures or compositions and the methods can, of course, also be employed for treating genetically modified (transgenic) plants, preferably useful plants, particularly preferably cotton, where such plants contain, for example, one or more foreign genes in order to obtain resistance against insecticides and/or herbicides.

The invention is illustrated in more detail by the examples, without being limited thereby.

EXAMPLES

1. Preparation of the Spray Liquors

A water application rate of 300 l/ha was initially charged. The components herbicide and adjuvant were then added with stirring at the application rates and in the manner stated in table 1, such that a homogeneous spray liquor was formed. Here, the active ingredients were employed as suspension concentrates. The adjuvant used was Agrotin® (Bayer CropScience).

2. Biological Tests 2.1 Test Method

Meanings of the abbreviations used below:

| | |
|---|---|
| g of a.i./ha = | gram of active ingredient/hectare |
| l/ha = | liter/hectare |
| TDZ = | thidiazuron |

Cotton seeds of the cultivar "Linda" were sown at a depth of 1 cm and cultivated in a climatized chamber (16 h of light, temperature during the day: 26° C., at night: 20° C.) until they had reached the 8-10 leaf stage.

The plants were treated on a laboratory spray track with spray liquors of thidiazuron and thidiazuron with combination partners. The water application rate for the spray application was 300 l/ha. After the treatment, the plants were returned to the climatized chamber.

1, 2 and 4 weeks after the application, the leaf drop effect was evaluated according to a scale from 0 to 100%:

0%=no noticeable effect compared to untreated plants

100%=all leaves have dropped.

2.2 Results for the Combinations of (A) TDZ with (B) Cyprosulfamide

The evaluations 2 weeks after application gave the results listed in table 1 which clearly show the synergistic effect for the leaf drop effect.

TABLE 1

| Components | Dose [g of a.i./ha] | Leaf drop [%] 2 weeks after application |
|---|---|---|
| untreated | | 6 |
| TDZ* | 35 | 67 |
| Cyprosulfamide* | 100 | 7 |
| Cyprosulfamide* | 200 | 0 |
| TDZ + Cyprosulfamide* | 35 + 100 | 87 |
| TDZ + Cyprosulfamide* | 35 + 200 | 79 |

*1 l of Agrotin was added to all spray liquors 2.3 Results for the Combinations of (A) TDZ with (B) Cyprosulfamide Over the Course of Time The evaluations gave the results listed in table 2 which clearly show the synergistic effect for the leaf drop effect, which continuously increases over the period of 1 to 4 weeks after application.

TABLE 2

| Components | Dose [g of a.i./ha] | Leaf drop [%] 1 week after application | Leaf drop [%] 2 weeks after application | Leaf drop [%] 4 weeks after application |
|---|---|---|---|---|
| untreated | | 0 | 0 | 0 |
| TDZ* | 25 | 37 | 56 | 63 |
| Cyprosulfamide | 200 | 0 | 0 | 0 |
| TDZ + Cyprosulfamide | 25 + 200 | 46 | 79 | 92 |

*0.2% by weight of Agrotin was added to the spray liquors

The invention claimed is:

1. A mixture, which comprises
(A) thidiazuron and
(B) at least one compound from the group of the N-phenylsulfonyl(het)arylamides, if appropriate also in salt form, of the formula below:

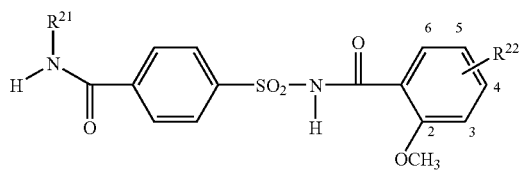

in which
$R^{21}$ is cyclopropyl and $R^{22}$ is H,
$R^{21}$ is cyclopropyl and $R^{22}$ is 5-Cl,
$R^{21}$ is ethyl and $R^{22}$ is H,
$R^{21}$ is isopropyl and $R^{22}$ is 5-Cl or
$R^{21}$ is isopropyl and $R^{22}$ is H,
wherein a ratio of the component (A) to the component (B) is 1:2 to 1:10.

2. The mixture as claimed in claim 1 which comprises, as component (B), cyprosulfamide.

3. A method for defoliating plants comprising applying a mixture according to claim 1 to a plant.

4. A method as claimed in claim 3, wherein the plant is a cotton plant.

5. A method as claimed in claim 4, wherein the cotton plant is a transgenic cotton plant.

6. A defoliant, which comprises
(A) thidiazuron and
(B) at least one compound selected from the group of the N-phenylsulfonyl(het)arylamides, if appropriate also in salt form, of the formula below:

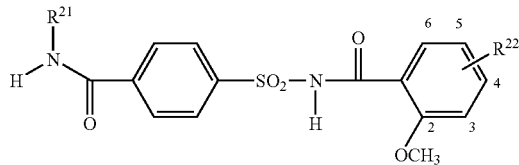

in which
$R^{21}$ is cyclopropyl and $R^{22}$ is H
$R^{21}$ is cyclopropyl and $R^{22}$ is 5-Cl,
$R^{21}$ is ethyl and $R^{22}$ is H,
$R^{21}$ is isopropyl and $R^{22}$ is 5-Cl or
$R^{21}$ is isopropyl and $R^{22}$ is H; and
(C) one or more formulation auxiliaries,
wherein a ratio of the component (A) to the component (B) is 1:2 to 1:10.

7. The defoliant as claimed in claim 6 which comprises, as component (B), cyprosulfamide.

8. A method for defoliating a plant comprising treating the plant with the defoliant as defined in claim 6.

9. The method as claimed in claim 8, wherein the plant is a cotton plant.

10. The method as claimed in claim 9, wherein the cotton plant is a transgenic cotton plant.

11. The mixture as claimed in claim 1, wherein component (B) comprises 4-isopropylaminocarbonyl-N-(2-methoxybenzoyl)benzenesulfonamide.

12. The mixture as claimed in claim 6, wherein component (B) comprises 4-isopropylaminocarbonyl-N-(2-methoxybenzoyl)benzenesulfonamide.

13. The mixture as claimed in claim 6, wherein component (C) comprises one or more of the formulation auxiliaries selected from the group consisting of adhesives, wetting agents, dispersants, emulsifiers, penetrants, preservatives, antifreeze agents, solvents, fillers, carriers, colorants, antifoams, evaporation inhibitors, pH regulators, and viscosity regulators.

14. A mixture, consisting essentially of:
(A) thidiazuron and
(B) at least one compound from the group of the N-phenylsulfonyl(het)arylamides, if appropriate also in salt form, of the formula below:

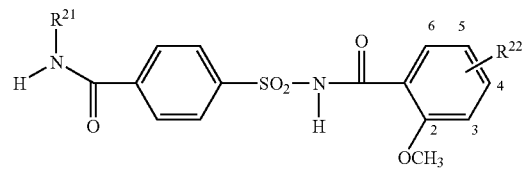

in which
$R^{21}$ is cyclopropyl and $R^{22}$ is H,
$R^{21}$ is cyclopropyl and $R^{22}$ is 5-Cl,
$R^{21}$ is ethyl and $R^{22}$ is H,
$R^{21}$ is isopropyl and $R^{22}$ is 5-Cl or
$R^{21}$ is isopropyl and $R^{22}$ is H,
wherein a ratio of the component (A) to the component (B) is 1:2 to 1:10.

* * * * *